United States Patent
Ad

(10) Patent No.: US 10,660,649 B2
(45) Date of Patent: May 26, 2020

(54) SYSTEM FOR OCCLUSION OF LEFT ATRIAL APPENDAGE

(71) Applicant: Niv Ad, North Bethesda, MD (US)

(72) Inventor: Niv Ad, North Bethesda, MD (US)

(*) Notice: Subject to any disclaimer, the term of this patent is extended or adjusted under 35 U.S.C. 154(b) by 241 days.

(21) Appl. No.: 15/661,580

(22) Filed: Jul. 27, 2017

(65) Prior Publication Data
US 2018/0000485 A1 Jan. 4, 2018

Related U.S. Application Data

(63) Continuation of application No. 14/809,473, filed on Jul. 27, 2015, now Pat. No. 9,737,309, which is a
(Continued)

(51) Int. Cl.
| | | |
|---|---|---|
| *A61B 17/122* | (2006.01) | |
| *A61B 17/128* | (2006.01) | |
| *A61B 17/12* | (2006.01) | |
| *A61B 17/00* | (2006.01) | |
| *A61B 17/30* | (2006.01) | |

(52) U.S. Cl.
CPC ......... *A61B 17/122* (2013.01); *A61B 17/128* (2013.01); *A61B 17/12013* (2013.01); *A61B 17/1285* (2013.01); *A61B 17/0057* (2013.01); *A61B 17/1204* (2013.01); *A61B 17/12022* (2013.01); *A61B 17/12031* (2013.01); *A61B 17/12099* (2013.01); *A61B 17/12122* (2013.01); *A61B 17/12136* (2013.01); *A61B 2017/00243* (2013.01); *A61B 2017/00557* (2013.01);
(Continued)

(58) Field of Classification Search
CPC .......... A61B 17/0057; A61B 17/12013; A61B 17/12022; A61B 17/12031; A61B 17/1204; A61B 17/12099; A61B 17/12122; A61B 17/12136; A61B 17/1285; A61B 2017/00243; A61B 2017/00557

See application file for complete search history.

(56) References Cited

U.S. PATENT DOCUMENTS

| 3,538,917 A | 11/1970 | Selker |
|---|---|---|
| 4,708,140 A | 11/1987 | Baron |
| (Continued) | | |

FOREIGN PATENT DOCUMENTS

| GB | 1268034 A | 3/1972 |
|---|---|---|
| WO | 03/096881 A2 | 11/2003 |
| (Continued) | | |

OTHER PUBLICATIONS

International Search Report and Written Opinion dated Oct. 18, 2018 for International Patent Application No. PCT-US2018-047233 filed Aug. 21, 2018, all pages.
(Continued)

*Primary Examiner* — Robert A Lynch
(74) *Attorney, Agent, or Firm* — Kilpatrick Townsend & Stockton LLP

(57) ABSTRACT

A device for occluding an atrial appendage includes a catheter-deliverable epicardial implant that is detachably secured to a delivery device. The implant includes an inflatable cuff that is positionable about the atrial appendage to an extent that, when adjustably inflated, the cuff physiologically occludes the atrial appendage. Such occlusion addresses health risks associated with atrial fibrillation and cardiac rhythm disorder.

20 Claims, 7 Drawing Sheets

Related U.S. Application Data continuation of application No. 13/168,009, filed on Jun. 24, 2011, now abandoned.

(60) Provisional application No. 61/358,127, filed on Jun. 24, 2010.

(52) U.S. Cl.
CPC ............... *A61B 2017/00566* (2013.01); *A61B 2017/306* (2013.01)

(56) References Cited

U.S. PATENT DOCUMENTS

| | | | |
|---|---|---|---|
| 4,800,879 | A | 1/1989 | Golyakhovsky et al. |
| 5,306,234 | A | 4/1994 | Johnson |
| 5,624,454 | A | 4/1997 | Palti et al. |
| 6,036,706 | A | 3/2000 | Morejohn et al. |
| 6,146,394 | A | 11/2000 | Moreiohn et al. |
| 6,290,674 | B1 | 9/2001 | Roue et al. |
| 6,458,100 | B2 | 10/2002 | Roue et al. |
| 6,488,689 | B1 | 12/2002 | Kaplan et al. |
| 6,561,969 | B2 | 5/2003 | Frazier et al. |
| 6,746,472 | B2 | 6/2004 | Frazier et al. |
| 7,011,682 | B2 | 3/2006 | Lashinski et al. |
| 7,115,110 | B2 | 10/2006 | Frazier et al. |
| 7,128,073 | B1 | 10/2006 | Van der Burg et al. |
| 7,152,605 | B2 | 12/2006 | Khairkhahan et al. |
| 7,226,458 | B2 | 6/2007 | Kaplan et al. |
| 7,318,829 | B2 | 1/2008 | Kaplan et al. |
| 7,344,543 | B2 | 3/2008 | Sra |
| 7,419,498 | B2 | 9/2008 | Opolski et al. |
| 7,549,983 | B2 | 6/2009 | Roue et al. |
| 7,566,336 | B2 | 7/2009 | Corcoran et al. |
| 7,591,818 | B2 | 9/2009 | Bertolero et al. |
| 7,597,704 | B2 | 10/2009 | Frazier et al. |
| 7,634,319 | B2 | 12/2009 | Schneider et al. |
| 7,645,285 | B2 | 1/2010 | Cosgrove et al. |
| 9,737,309 | B1 | 8/2017 | Ad |
| 2002/0049457 | A1 | 4/2002 | Kaplan et al. |
| 2002/0072759 | A1 | 6/2002 | Fry |
| 2003/0199923 | A1 | 10/2003 | Khairkhahan et al. |
| 2003/0225443 | A1 | 12/2003 | Kiran et al. |
| 2004/0044361 | A1 | 3/2004 | Frazier et al. |
| 2004/0230222 | A1 | 11/2004 | Van der Burg et al. |
| 2005/0033287 | A1 | 2/2005 | Sra |
| 2005/0149069 | A1 | 7/2005 | Bertolero et al. |
| 2005/0177182 | A1 | 8/2005 | Van der Burg et al. |
| 2005/0192531 | A1 | 9/2005 | Birk |
| 2006/0167444 | A1 | 7/2006 | Swanson |
| 2006/0206148 | A1 | 9/2006 | Khairkhahan et al. |
| 2006/0253129 | A1 | 11/2006 | Liddicoat et al. |
| 2007/0016228 | A1 | 1/2007 | Salas |
| 2007/0021761 | A1 | 1/2007 | Phillips |
| 2007/0043344 | A1 | 2/2007 | McAuley |
| 2007/0073313 | A1 | 3/2007 | Liddicoat et al. |
| 2007/0250086 | A1 | 10/2007 | Wiley et al. |
| 2008/0033457 | A1 | 2/2008 | Francischelli et al. |
| 2008/0039879 | A1 | 2/2008 | Chin et al. |
| 2008/0269788 | A1 | 10/2008 | Phillips |
| 2009/0163846 | A1 | 6/2009 | Aklog et al. |
| 2009/0240269 | A1 | 9/2009 | Denis |
| 2010/0145361 | A1 | 6/2010 | Francischelli et al. |
| 2011/0009853 | A1 | 1/2011 | Bertolero et al. |
| 2014/0364901 | A1 | 12/2014 | Kiser et al. |
| 2017/0042550 | A1 | 2/2017 | Chakraborty et al. |
| 2017/0196568 | A1 | 7/2017 | Gross et al. |

FOREIGN PATENT DOCUMENTS

| | | |
|---|---|---|
| WO | 2009/106907 A1 | 9/2009 |
| WO | 2014-190317 A2 | 11/2014 |

OTHER PUBLICATIONS

Non-Final Office Action dated Jul. 9, 2019 in U.S. Appl. No. 15/681,812, all pages.

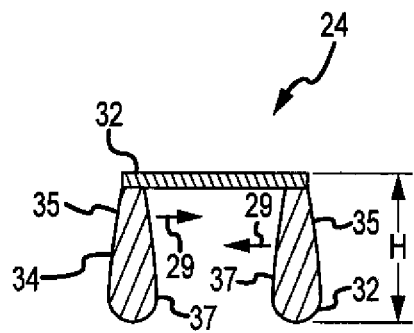
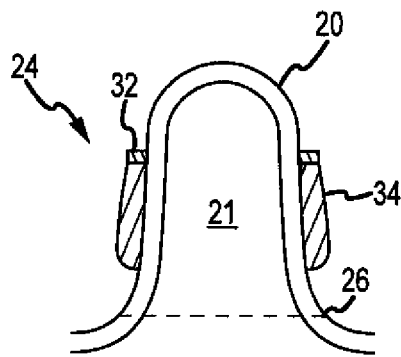
FIG.5A    FIG.5B
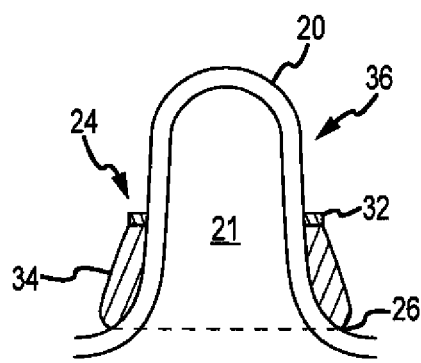
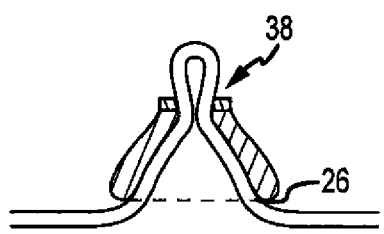
FIG.5C    FIG.5D

SYSTEM FOR OCCLUSION OF LEFT ATRIAL APPENDAGE

CROSS-REFERENCE TO RELATED APPLICATIONS

This application is a continuation of U.S. patent application Ser. No. 14/809,473, filed on Jul. 27, 2015 and entitled "System for Occlusion of Left Atrial Appendage", which is a continuation of U.S. patent application Ser. No. 13/168,009, filed on Jun. 24, 2011 and entitled "System for Occlusion of Left Atrial Appendage", which itself claims priority to U.S. Provisional Application Ser. No. 61/358,127, filed on Jun. 24, 2010 and entitled System for Occlusion of Left Atrial Appendage", the contents of which are being incorporated herein in their entirety.

FIELD OF THE INVENTION

The present invention relates to devices and methods for occluding lumens in internal soft body tissue, and more particularly to devices and methods for physiologically occluding the left atrial appendage ("LAA"). The present invention involves a permanent or semi-permanent implant which epicardially occludes the LAA, and is adjustable so as to occlude the LAA from its base.

BACKGROUND OF THE INVENTION

Atrial fibrillation ("AF") is a common cardiac rhythm disorder ("cardiac arrhythmia") and is characterized by a rapid chaotic heartbeat in which the upper chambers of the heart known as the atria quiver rapidly instead of beating in a steady rhythm. This rapid quivering reduces the heart's ability to properly function as a pump.

Atrial fibrillation typically increases the risks of thromboembolic stroke and congestive heart failure. Quality of life is also impaired by common AF symptoms such as palpitations, chest pain, fatigue, and dizziness. The irregular heartbeat associated with AF causes blood to pool in the left atrial appendage, allowing clots to accumulate over time. From time to time, clots may dislodge from the left atrial appendage, and may enter various circulation tracks causing strokes, myocardial infarction, limb ischemia, and other vascular problems.

A number of approaches have been implemented to address the health risks associated with AF. Among such techniques, surgical procedures for closing (occluding) the left atrial appendage (LAA) have been proposed. Some of such procedures involve open chest wall midstemotomy procedures while others may access the pericardial space through a thoracotomy or from a sub-xiphoid access point. In such approaches, a physical device is typically employed to cinch or compress the LAA.

Conventional LAA closure devices, however, are difficult to precisely position at the LAA, and therefore result in incomplete occlusion of the LAA, as the surgical closure point is oftentimes spaced from the base of the LAA. Moreover, conventional closure devices lack simple repositioning and adjustment capabilities, such that attempts to physiologically completely occlude the LAA frequently fail.

It is therefore an object of the invention to provide a tissue occlusion device which facilitates placement and ultimate closure of the left atrial appendage at its base.

It is another object of the present invention to provide an atrial appendage closure device having adjustment capabilities to facilitate re-positioning of the device at the atrial appendage, and complete occlusion of the appendage at its base.

BRIEF DESCRIPTION OF THE DRAWINGS

FIG. 5A is an isolation elevational view of a portion of the atrial appendage occlusion device illustrated in FIGS. 1 and 2;

FIG. 5B is a schematic view of an atrial appendage occlusion device in engagement with a left atrial appendage;

FIG. 5C is a schematic view of an atrial appendage occlusion device in engagement with a left atrial appendage;

FIG. 5D is a schematic view of an atrial appendage occlusion device in engagement with a left atrial appendage in a closed condition;

DESCRIPTION OF THE INVENTION

The objects and advantages enumerated above together with other objects, features, and advances represented by the present invention will now be presented in terms of detailed embodiments described with reference to the attached drawing figures which are intended to be representative of various embodiments of the invention. Other embodiments and aspects of the invention are recognized as being within the grasp of those having ordinary skill in the art.

Figure 1:
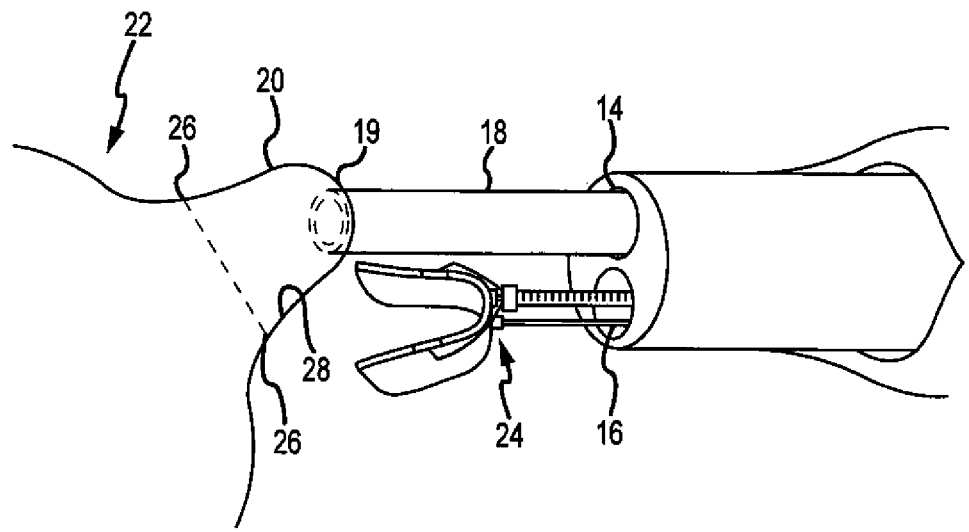
FIG. 1 is a schematic diagram of an atrial appendage occlusion device of the present invention.

With reference now to the drawings, and first to FIG. 1, an atrial appendage occlusion device 10 includes a multiple lumen delivery device 12, such as a steerable catheter, as is well known in the art. In one embodiment, delivery device 12 includes first and second lumens 14, 16 for simultaneously delivering a plurality of devices to, for example, the left atrial appendage (LAA) 20 of a left atrium 22 of a human heart. In the illustrated embodiment, a grasping device 18 may be delivered through first lumen 14, while an implant 24 may be delivered through second lumen 16 of delivery device 12.

One aspect of the present invention provides for laparoscopic/percutaneous transport of delivery device 12 to LAA 20. In some embodiments, delivery device 12 is a distally steerable catheter for minimally invasive introduction to the pericardial space through the pleural or sub-xiphoid spaces using a seldinger technique. In such a manner, implant 24 of the present invention may be delivered to the LAA without the need for midsternotomy. It is to be understood, however, that the device 10 of the present invention may be useful for direct access to the LAA in cases where the patient is undergoing a midsternotomy for other surgical procedures. In either scenario, device 10 is arranged for an epicardial treatment of the LAA.

Once device 10 has been introduced into the patient, advancement and positioning may be performed through conventional imaging techniques, such as thoracoscopic or fluoroscopic imaging. In some embodiments, delivery device 12 may be compatible with imaging scopes which may be introduced through a selected lumen 14, 16 thereof.

As described above, the device of the present invention is arranged to occlude, for example, LAA 20 by pinching, cinching, crimping, clamping, compressing, or otherwise closing base 26 of LAA 20. In one embodiment, closing or "occluding" LAA 20 at base 26 is accomplished by securing an inner surface 28 of LAA 20 to itself substantially at base 26. Such securement effectively fluidly seals off an interior of LAA 20 from left atrium 22, and prevents blood clots from embolizing from within LAA 20 to left atrium 22. In some embodiments, the occlusion is of a character to cut off nutrient-providing blood supply to the tissue of LAA 20, thereby eventually resulting in necrosis and/or obliteration of LAA 20. In the illustrated embodiment, a means for effectuating occlusion of LAA 20 is implant 24, which may be detachably secured to delivery device 12 to remain indefinitely after delivery device 12 is removed from the patient.

In the embodiment illustrated in FIG. 1, a grasping device 18 may be employed to grasp and releasably hold LAA 20 to facilitate positioning and engagement of implant 24 at LAA 20. Grasping device 18 may typically comprise a conventional grasping tool, such as a suction tube which establishes negative pressure at a distal end 19 thereof, the negative pressure being suitable to releasably retain tissue, such as LAA 20 at distal end 19. Alternative grasping tools include thoracoscopic forceps and the like.

Figure 2:
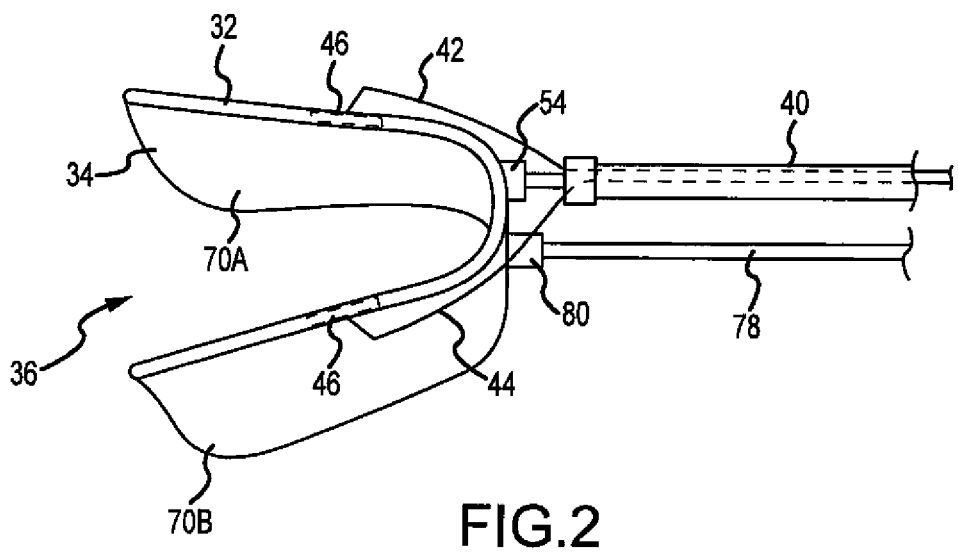
FIG. 2 is an isolation view of a portion of the atrial appendage occlusion device illustrated in FIG. 1.
Figure 2A:
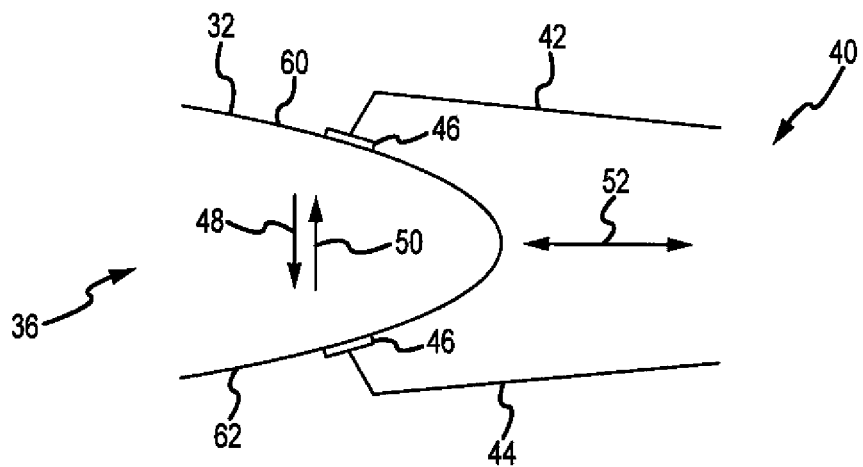
FIG. 2A is a top schematic view of a portion of the atrial appendage occlusion device illustrated in FIGS. 1 and 2 in an open condition.
Figure 2B:
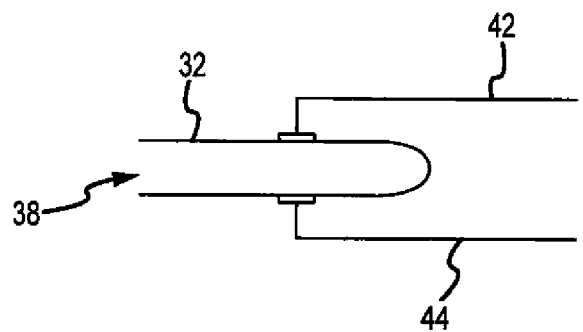
FIG. 2B is a top schematic view of a portion of the atrial appendage occlusion device illustrated in FIGS. 1 and 2 in a closed condition.

An enlarged view of implant 24 is illustrated in FIG. 2, wherein implant 24 includes a clamp 32 and an inflatable cuff 34 attached to clamp 32. In some embodiments, clamp 32 is selectively adjustable between an open, unclamped condition 36 (as illustrated in FIG. 2), and a closed, clamped position 38. Applicant contemplates a variety of mechanisms for selectively adjusting clamp 22 between the open and closed conditions 36, 38. For example, implant 24 may utilize a control arm 40, which incorporates the dual purpose of physically manipulating the spatial position of clamp 32, as well as selectively adjusting clamp 32 between open and closed conditions 36, 38. An example mechanism for effectuating such selective adjustment is illustrated in FIGS. 2A and 2B. In the illustrated embodiment, control arm 40 includes actuators 42, 44, which are detachably secured to clamp 32 at securement points 46. First and second actuators 42, 44 may be proximally controlled to move relative to one another generally along directions 48, 50 so as to adjust clamp 32 between open and closed conditions 36, 38. First and second actuators 42, 44 are also capable of rotating clamp 32 about an axis 52, and for turning clamp 32 into alignment with LAA 20. Such alignment enables first and second prongs 60, 62 to be placed at least partially about LAA 20.

In addition to, or in place of, the detachable securement of first and second actuators 42, 44 at securemented points 46, control arm 40 may include a detachable link 54 which may be severed, opened, or otherwise released so as to disengage clamp 32 from control arm 40. Applicant contemplates a variety of mechanisms for detachably securing clamp 32 to control arm 40, with some of such mechanisms being conventionally understood by those of ordinary skill in the art.

Figure 3:
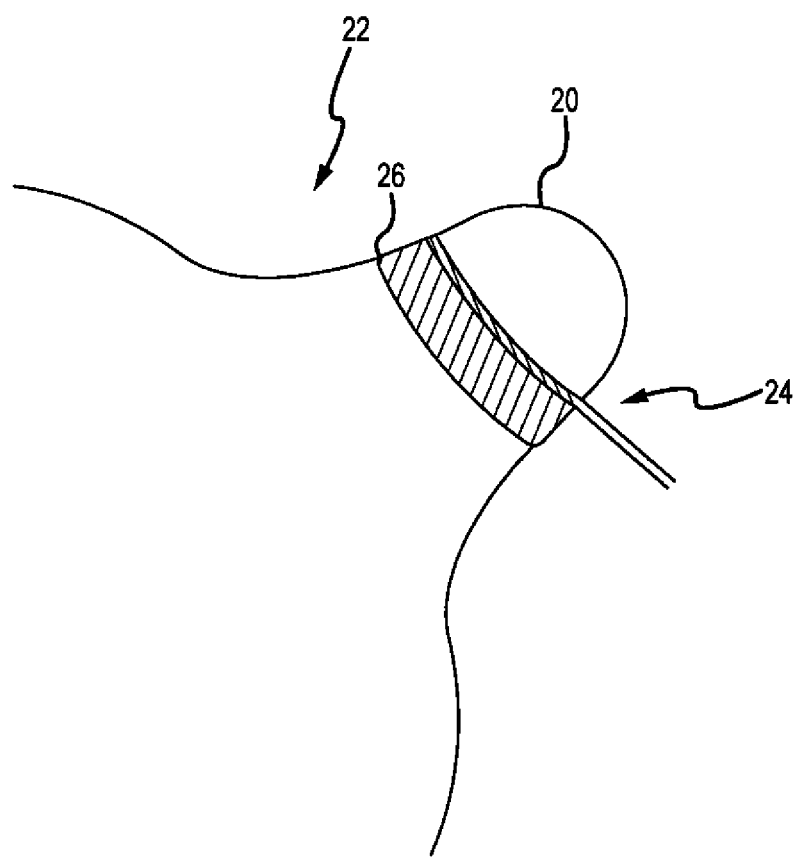
FIG. 3 is a schematic diagram of an atrial appendage occlusion device of the present invention engaged with a left atrial appendage.

As indicated above, implant 24 may be positioned at LAA 20 through thoracoscopic or fluoroscopic guidance. FIG. 3 illustrates an engagement of implant 24 with LAA 20. Implant 24 may be manipulated by, for example, first and second actuators 42, 44, so that first and second prongs 60, 62 of clamp 32 are positioned at substantially opposed sides 68, 70 of LAA 20, and about at least a portion of LAA 20.

Figure 3A:
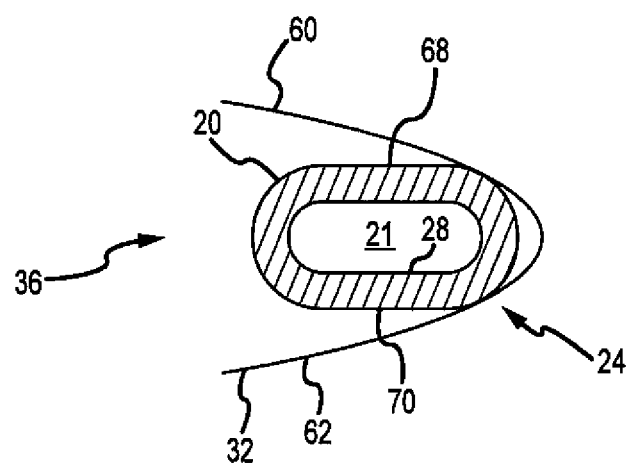
FIG. 3A is a schematic view of an atrial appendage occlusion device engaged with a left atrial appendage in an open condition.
Figure 3B:
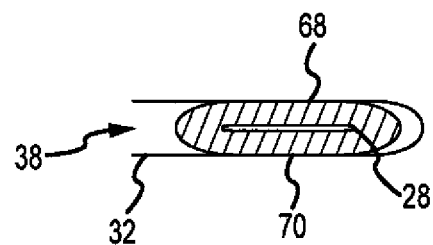
FIG. 3B is a schematic view of an atrial appendage occlusion device engaged with a left atrial appendage in a closed condition.

As illustrated in the schematic views of FIGS. 3A and 3B, LAA 20 includes a lumen 21 defined by inner surface 28. Implant 24 is engaged with LAA 20 initially while in an open condition 36, with first and second prongs 60, 62 of clamp 32 being positioned at substantially opposed sides 68, 70 of LAA 20. When clamp 32 is manipulated as described above from open condition 36 to closed condition 38, as illustrated in FIG. 3B, lumen 21 of LAA 20 may be substantially closed through the pressing together of opposed sides 68, 70 of LAA 20 to an extent that inner surface 28 is in contact with itself. The placement of clamp 32 in closed condition 38 may occlude LAA 20 by completely closing lumen 21. However, as described in greater detail hereinbelow, clamp 32 primarily serves as an anchoring element for inflatable cuff 34, such that inflatable cuff 34 is positioned and oriented to physiologically occlude LAA 20 at base 26.

In one aspect of the present invention, clamp 32 may be selectively adjusted between open and closed positions 36, 38 to not only anchor implant 24 at LAA 20, but to also facilitate the repositioning of implant 24 at LAA 20. For example, imaging techniques such as fluoroscopy and echocardiography may be utilized to assess whether inflatable cuff 34 is properly positioned to physiologically occlude LAA 20 at base 26. In the event that it is determined that the initial placement of implant 24 is incorrect for a preferred occlusion of LAA 20, an adjustment mechanism, such as first and second actuators 42, 44 of control arm 40 may reopen clamp 32 from closed condition 38 to open condition 36, and thereafter reposition clamp 32 at LAA 20. Once the position of clamp 32 (and implant 24) has been adjusted, clamp 32 may again be modified from open condition 36 to closed condition 38 to securely anchor implant 24 at LAA 20. Such adjustability of clamp 32, and correspondingly implant 24, is facilitated through the detachable connection of control arm 40 to clamp 32. The detachable connection, as described above, enables proximal control to repeatedly adjust clamp 32 between open and closed conditions 36, 38, including from open condition 36 to closed condition 38, and from closed condition 38 to open condition 36. Such adjustment of clamp 32 may be repeated several times if necessary to appropriately position and orient implant 24 at LAA 20.

Clamp 32 may be fabricated from a variety of biocompatible materials, such as stainless steel, titanium, and other metallic, alloy, and non-metallic materials. In some embodiments, clamp 32 may be formed of a resilient material, thereby continuing to apply direct pressure to LAA 20 enclosed within clamp 32 in closed condition 28. Because clamp 32 primarily serves as an anchoring device, clamp 32 need not be of specific structural capacity, and may therefore exhibit a relatively low profile for ease of delivery and placement at LAA 20.

Figure 4A:
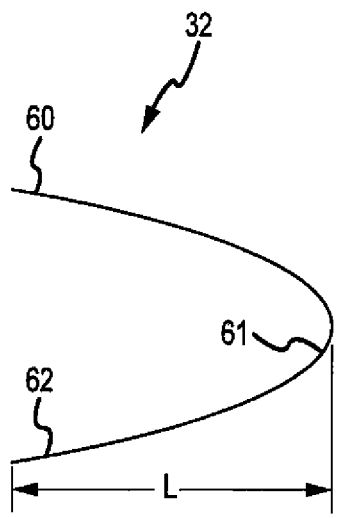
FIG. 4A is an isolation view of a portion of the atrial appendage occlusion device illustrated in FIGS. 1 and 2 in an open condition.
Figure 4B:
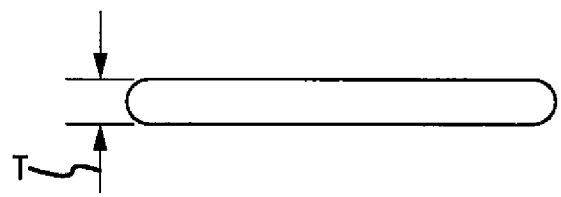
FIG. 4B is an isolation view of a portion of the atrial appendage occlusion device illustrated in FIGS. 1 and 2 in a closed condition.

As illustrated in FIGS. 4A and 4B, clamp 32 includes first and second prongs 60, 62 emanating from central portion 61. First and second prongs 60, 62 may be the same or different curvatures forming various shapes, including an opening with tapered ends, oval, ovoid, crescent, etc. Prong length "L" may be equal or different as between first and second prongs 60, 62, and may be provided in various sizes as physiologically appropriate. For example, prong length "L" may be between about 1-5 cm, though other sizes are contemplated as being useful in the present invention. Moreover, prong thickness "T" may be even or uneven along first and second prongs 60, 62, and may be between, for example, about 0.1-5 mm.

Clamp 32 may also include tissue engaging projections and fasteners, such as spikes, staples, rivets, sutures, and clips extending from one or both of first and second prongs 60, 62. The tissue fasteners may be formed of a resilient, elastic, superelastic, metallic, alloy, or non-metallic material. The tissue fasteners may be integrally formed with clamp 32, mounted within clamp 32, or mounted within a device that may be attached to clamp 32.

The repositionability of clamp 32 is advantageous for precisely positioning inflatable cuff 34 at LAA 20, such that inflation of cuff 34 physiologically occludes LAA 20 at base 26. For the purposes hereof, the term "physiologically occludes" is intended to mean the substantially complete closure or occlusion of lumen 21 of LAA 20 to an extent appropriate to prevent the formation of clot and the release of emboli from the appendage. Therefore, "physiological occlusion" may include any closure of LAA 20 which is effective in the prevention of clot formation and the release of emboli therefrom, and need not comprise the closure of the entirety of lumen 21 of LAA 20. In some embodiments, "physiologically occludes" may refer to a closure of lumen 21 at or near base 26 with such closure constituting intimate contact of inner surface 28 at or near base 26 to an extent appropriate to prevent blood flow into and out from LAA 20.

Inflatable cuff 34 includes one or more portions 70A, 70B that may be selectively inflated with a fluid, such as saline, to inwardly press upon LAA 20 to an extent appropriate to physiologically occlude LAA 20. To selectively inflate inflatable cuff 34, implant 24 includes a fluid supply tube 78 that is detachably secured to inflatable cuff 34. Fluid supply tube 78 may be configured for selectively conveying pressurized fluid such as saline to inflatable cuff 34 through a one way valve 80 which permits fluid flow into, but not out from, inflatable cuff 34. Fluid supply tube 78 is preferably deliverable along with implant 24 through a lumen 16 of delivery device 12.

In some embodiments, inflatable cuff 34 defines one or more balloon structures defining respective portions 70A, 70B, with the balloon structures employing a resiliently elastic skin which may be resiliently expanded upon inflating fluid flow from fluid supply tube 78 into respective chambers thereof. As illustrated in FIG. 5A, inflatable cuff 34 may include relatively rigid outer walls 35 with relatively elastic and non-rigid inner walls 37. In such a manner, inflation of inflatable cuff 34 causes expansion of inflatable cuff 34 inwardly along direction arrows 39. Such inward expansion of inflatable cuff 34 effectuates the occlusion of LAA 20.

Inflatable cuff 34 may be fabricated from a variety of materials to provide the functionality described above. In particular, inflatable cuff 34 may include a skin layer 82 which is manufactured from one or more materials to provide zoned characteristics. As described above, a first material for skin layer 82 may be substantially rigid at outer surface 35, while a different material may be provided at an inner surface 37. In other embodiments, reinforcement materials or devices may be employed to promote inward expansion of cuff 34 upon inflation thereof. Such reinforcement materials or devices may be disposed at or adjacent to outer surface 35 of inflatable cuff 34 to limit outwardly-directed expansion.

Inflatable cuff 34 may be secured to clamp 32 at one or more points along clamp 32. In some embodiments, inflatable cuff 34 is secured to the entire length of clamp 32. In other embodiments, however, inflatable cuff 34 may extend only partially along clamp 32, and may include discontinuous portions along clamp 32. A variety of securement mechanisms are contemplated by the present invention to secure inflatable cuff 34 to clamp 32. Example mechanisms include adhesives, fasteners, and other mechanisms, including conventional mechanisms for securing inflatable cuff 34 to clamp 32.

Inflatable cuff 34 may include one or more distinct chambers that are sequentially or simultaneously filled with inflation fluid supplied through fluid supply tube 78. In one embodiment, for example, inflatable cuff 34 may include a plurality of chambers which are filled through an "overflow" concept in which a secondary chamber is filled only after a primary chamber is completely filled with fluid. In some embodiments, each portion 70A, 70B of inflatable cuff 34 may be filled with between about 1-10 cc of fluid.

Figure 5E:
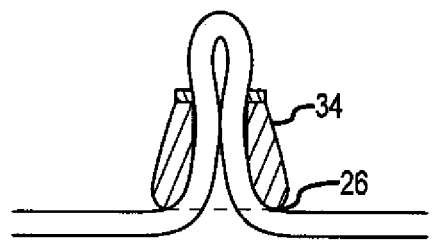
FIG. 5E is a schematic view of an atrial appendage occlusion device in occlusive engagement with a left atrial appendage.

An occlusion sequence utilizing implant 24 is illustrated in FIGS. 5B-5E, in which implant 24 is placed about LAA 20 in an open condition 36. Positioning of implant 24 at LAA 20 may be verified through echocardiography and fluoroscopy. FIG. 5B illustrates an improper positioning of implant 24, in that inflatable cuff 34 does not extend to base 26 of LAA 20, where occlusion is desired. In one embodiment, clamp 32 may be adjusted to a closed condition 38 at the position illustrated in FIG. 5B, followed by position verification through echocardiography and/or fluoroscopy. When it is determined that the position and/or orientation of implant 24 is incorrect, clamp 32 may be re-adjusted to an open condition 36 for re-positioning of implant 24, as described above.

Implant 24 may be re-positioned, as illustrated in FIG. 5C. Here, inflatable cuff 34 extends substantially to base 26 of LAA 20. Confirmation of such appropriate position and orientation may be performed, for example, subsequent to adjustment of clamp 32 to a closed condition 38, such as is illustrated in FIG. 5D.

Once the appropriate position of implant 24 has been confirmed, fluid is directed through fluid supply tube 78, and through one-way valve 80 into inflatable cuff 34 to thereby expand inflatable cuff 34 to an extent appropriate to physiologically occlude LAA 20 at base 26. FIG. 5E illustrates such occlusion subsequent to inflation of inflatable cuff 34. Sufficient occlusion of LAA 20 may be confirmed through echocardiography and/or fluoroscopy. If, for example, further closure of LAA 20 is required to accomplish physiological occlusion, additional fluid may be added to inflatable cuff 34 through fluid supply tube 78.

Figure 5F:
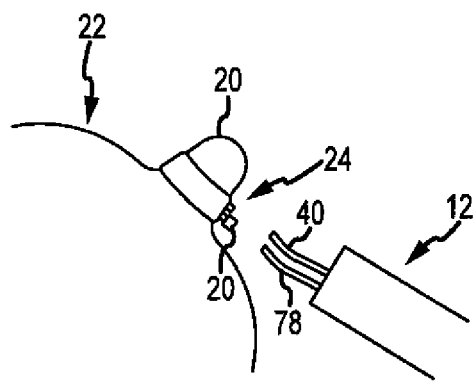
FIG. 5F is a schematic view of an atrial appendage occlusion device with an implant portion separated from a delivery device.

Once appropriate occlusion has been confirmed, control arm 40 may be detached from clamp 32 as described above. Moreover, fluid supply tube 78 may be separated from inflatable cuff 34, preferably upstream from one-way valve 80 so as to maintain fluid pressure within inflatable cuff 34. An illustration of implant 24 at LAA 20 subsequent to separation from control arm 40 and fluid supply tube 78 is shown in FIG. 5F. A variety of mechanisms are contemplated for separating fluid supply tube 78 from inflatable cuff 34. In one embodiment, a thoracoscopic scissor may be guided through delivery device 12 to cut fluid supply tube 78 at a location proximal to one-way valve 80. Subsequent to the separation, the thoracoscopic scissor, fluid supply tube 78, and control arm 40 may be withdrawn through respective lumens 14, 16 of delivery device 12, and the delivery device 12 may thereafter be withdrawn from the patient. Consequently, implant 24 may be left at LAA 20 indefinitely to ensure physiological occlusion thereof.

In one embodiment, inflatable cuff 34 is detachably secured to clamp 32, such that subsequent to confirmation of physiological occlusion of LAA 20 by inflatable cuff 34, clamp 32 may be detached from inflatable cuff 34, and withdrawn from the procedure site through delivery device 12. In such an embodiment, only inflatable cuff 34 is left at LAA 20 following the occlusion procedure. Therefore, it is to be understood that clamp 32 primarily acts as an anchoring mechanism, while inflatable cuff 34 performs the occlusion of LAA 20. Inflatable cuff 34 may assume a variety of configurations, and in one embodiment may have a height "H" of about 0.2-2 cm. Other sizes, however, of inflatable cuff 34 may be employed in implant 24 of the present invention.

For the purposes hereof, the term "cuff" is not intended to be exclusive of the various inflatable or otherwise expandable bodies useful in the present application. To that end, other terms may be interchangeably utilized to describe inflatable cuff 34. Example alternative terms include bladder, balloon, diaphragm, vessel, skirt, tube, and the like. Moreover, inflatable cuff 34 may be selectively and adjustably expandable through means other than inflation, including various mechanical expansion means to constrict the LAA 20 to an occlusive extent.

The invention has been described herein in considerable detail in order to comply with the patent statutes, and to provide those skilled in the ark with the information needed to apply the novel principles and to construct and use embodiments of the invention as required. However, it is to be understood that the invention can be carried out by different methods/devices, and that various modifications can be accomplished without departing from the scope of the invention itself.

What is claimed is:

1. An epicardial implant, comprising:
a positioning device defining an open interior having a central axis, wherein the positioning device is configured to be detachably coupled with an implant delivery device such that the positioning device may be detached from the implant delivery device after the epicardial implant is in place about the atrial appendage, and wherein the open interior of the positioning device receives a portion of the atrial appendage; and
at least one expandable cuff coupled with the positioning device such that the at least one expandable cuff is positioned outside of the open interior of the positioning device;
wherein the positioning device is configured to selectively move the expandable cuff toward and away from an atrial appendage to position the expandable cuff in a desired position relative to the atrial appendage;
wherein the at least one expandable cuff is expandable inwardly toward the central axis of the open interior of the positioning device following placement of the expandable cuff into the desired position; and
wherein the at least one expandable cuff is configured to physically occlude a base of the atrial appendage when expanded.

2. The epicardial implant of claim 1, wherein:
the positioning device comprises a first prong that is coupled with a second prong at a hinge that is configured to adjust a distance between the first prong and the second prong, wherein a space between the first prong and the second prong defines the open interior of the positioning device.

3. The epicardial implant of claim 1, wherein:
the at least one expandable cuff comprises a plurality of distinct chambers that are sequentially or simultaneously filled with a fluid to expand the at least one expandable cuff.

4. The epicardial implant of claim 3, wherein:
the fluid comprises saline.

5. The epicardial implant of claim 1, wherein:
the at least one expandable cuff comprises at least one rigid outer wall and at least one elastic and non-rigid inner wall.

6. The epicardial implant of claim 1, further comprising:
a one-way valve that is configured to allow fluid to enter an interior of the at least one expandable cuff to expand the at least one expandable cuff.

7. The epicardial implant of claim 1, wherein:
the at least one expandable cuff comprises an inflatable balloon.

8. An epicardial implant, comprising:
a positioning device defining an open interior between a first prong and a second prong, the open interior having a central axis, wherein the first prong and the second prong are movable between an open position and a closed position, wherein the positioning device is configured to be releasably coupled with an implant delivery device, and wherein the open interior of the positioning device receives a portion of the atrial appendage:
at least one expandable cuff that is coupled with the positioning device such that the at least one expandable cuff is positioned outside of the open interior of the positioning device and that is expandable inwardly toward the central axis of the open interior of the positioning device, wherein the at least one expandable cuff is configured to physically occlude a base of an atrial appendage when expanded; and
a one-way valve that is configured to allow fluid to enter an interior of the at least one expandable cuff to expand the at least one expandable cuff.

9. The epicardial implant of claim 8, wherein:
the at least one expandable cuff comprises a first expandable cuff that is coupled with the first prong and a second expandable cuff that is coupled with the second prong.

10. The epicardial implant of claim 8, wherein:
the at least one expandable cuff comprises at least one rigid outer wall and at least one elastic and non-rigid inner wall.

11. The epicardial implant of claim 8, wherein:
the at least one expandable cuff comprises an inflatable balloon.

12. The epicardial implant of claim 8, wherein:
the one-way valve is configured to be detachably coupled with a fluid supply tube of a delivery device.

13. The epicardial implant of claim 8, wherein:
the positioning device is repeatedly manipulatable between the open position and the closed position such that the positioning device is repositionable relative to the atrial appendage.

14. The epicardial implant of claim 8, wherein the positioning device further comprises:
one or more tissue engaging features.

15. A method for treating an atrial appendage, the method comprising:
providing an epicardial implant, the epicardial implant comprising:
a positioning device defining an open interior having a central axis; and
at least one expandable cuff that is coupled with the positioning device such that the at least one expandable cuff is positioned outside of the open interior of the positioning device and that is expandable inwardly toward the central axis of the open interior of the positioning device;
positioning the epicardial implant around an external surface of the atrial appendage such that a base of the atrial appendage is disposed in the open interior of the positioning device; and
expanding the at least one expandable cuff inwardly toward the central axis of the open interior of the positioning device to an extent sufficient to physically occlude the atrial appendage at the base.

16. The method for treating an atrial appendage of claim 15, wherein:
expanding the at least one expandable cuff comprises introducing a fluid into an interior of the at least one expandable cuff via a fluid supply tube.

17. The method for treating an atrial appendage of claim 16, wherein:
the fluid is introduced into the at least one expandable cuff via a one-way valve that interfaces with the fluid supply tube.

18. The method for treating an atrial appendage of claim 15, wherein:
positioning the epicardial implant comprises closing the positioning device around the base of the atrial appendage such that the base of the atrial appendage is anchored within the open interior of the positioning device.

19. The method for treating an atrial appendage of claim 15, further comprising:
upon expanding the at least one expandable cuff, disengaging the epicardial implant from a delivery device.

20. The method for treating an atrial appendage of claim 15, further comprising:
prior to positioning the epicardial implant, grasping the atrial appendage using a grasping device of a delivery device.

* * * * *